(12) United States Patent
Burcher et al.

(10) Patent No.: US 8,734,352 B2
(45) Date of Patent: May 27, 2014

(54) SPATIALLY-FINE SHEAR WAVE DISPERSION ULTRASOUND VIBROMETRY SAMPLING

(75) Inventors: Michael R. Burcher, Cambridge (GB); Hua Xie, Ossining, NY (US); Anna Teresa Fernandez, Falls Church, VA (US); Jean-Luc Robert, White Plains, NY (US)

(73) Assignee: Koninklijke Philips N.V., Eindhoven (NL)

( * ) Notice: Subject to any disclaimer, the term of this patent is extended or adjusted under 35 U.S.C. 154(b) by 60 days.

(21) Appl. No.: 13/383,471

(22) PCT Filed: Jun. 23, 2010

(86) PCT No.: PCT/IB2010/052863
§ 371 (c)(1),
(2), (4) Date: Jan. 11, 2012

(87) PCT Pub. No.: WO2011/007278
PCT Pub. Date: Jan. 20, 2011

(65) Prior Publication Data
US 2012/0116220 A1    May 10, 2012

Related U.S. Application Data

(60) Provisional application No. 61/226,485, filed on Jul. 17, 2009.

(51) Int. Cl.
*A61B 8/00* (2006.01)
(52) U.S. Cl.
USPC .......................................... 600/442; 600/437
(58) Field of Classification Search
USPC ................................ 600/437–469
See application file for complete search history.

(56) References Cited

U.S. PATENT DOCUMENTS

| | | | |
|---|---|---|---|
| 5,921,931 A | 7/1999 | O'Donnell et al. | |
| 6,390,980 B1 | 5/2002 | Peterson et al. | |
| 7,753,847 B2 * | 7/2010 | Greenleaf et al. | 600/438 |
| 7,785,259 B2 * | 8/2010 | Zheng et al. | 600/438 |

(Continued)

FOREIGN PATENT DOCUMENTS

| | | |
|---|---|---|
| WO | 2006113445 A1 | 10/2006 |
| WO | 2007144520 A1 | 12/2007 |
| WO | 2008139245 A1 | 11/2008 |

OTHER PUBLICATIONS

C. Passmann et al., "A 100-MHz ultrasound imaging system for dermatologic an opthalmologic diagnostics," IEEE Trans. Ultrasonics, Ferroelectrics and Frequency Control, vol. 43, No. 4, pp. 545-552 (1996).

(Continued)

*Primary Examiner* — Sanjay Cattungal (57) ABSTRACT

Shear wave dispersion ultrasound vibrometry (SDUV) is implemented in some embodiments to form, from a single tracking pulse, in-parallel-directed receive lines (411-426) for making measurements of a monochromatic shear wave. In some embodiments, sampling is performed, over spatial locations by means of passes over the locations, in an interlaced pattern (600) for making measurements of the wave. In some embodiments, measurements are made of the wave and to the measurements are applied a bank of filters (S724) that are tuned to respective candidate wave speeds, all without the need to determine a difference between wave phases at different spatial locations (451-454).

10 Claims, 7 Drawing Sheets

(56) References Cited

U.S. PATENT DOCUMENTS

| | | |
|---|---|---|
| 2002/0143253 A1 | 10/2002 | Robinson |
| 2004/0167403 A1 | 8/2004 | Nightingale et al. |
| 2005/0165306 A1* | 7/2005 | Zheng et al. ............... 600/437 |
| 2006/0122506 A1 | 6/2006 | Davies et al. |
| 2007/0038095 A1* | 2/2007 | Greenleaf et al. ........... 600/438 |
| 2009/0069693 A1 | 3/2009 | Burcher et al. |
| 2011/0063950 A1* | 3/2011 | Greenleaf et al. ............. 367/87 |
| 2011/0184287 A1* | 7/2011 | McAleavey ................. 600/438 |
| 2011/0263978 A1* | 10/2011 | Chen et al. .................. 600/438 |
| 2011/0319756 A1* | 12/2011 | Zheng et al. ................ 600/438 |
| 2012/0123262 A1* | 5/2012 | Xie et al. .................... 600/438 |
| 2012/0226158 A1* | 9/2012 | Greenleaf et al. ........... 600/438 |
| 2013/0024136 A1* | 1/2013 | Gallippi et al. ................ 702/41 |

OTHER PUBLICATIONS

M. W. Urban et al., "Error Estimates in Shear Wave Speed and Tissue Material Properties in Shear Wave Dispersion Ultrasound Vibrometry", 2007 IEEE Ultrasonics Symposium, pp. 664-667.

Y. Yamakoshi et al., "Ultrasonic Imaging of Internal Vibration of Soft Tissue Under Forced Vibration", IEEE Transactions on Ultrasonics, Ferroelectrics and Frequency Control, vol. 37, No. 2, pp. 45-53, 1990.

M. Palmeri et al., "On the Thermal Effects Associated with Radiation Force Imaging of Soft Tissue", IEEE Transactions on Ultrasonics, Ferroelectrics and Frequency Control, vol. 51, No. 5, pp. 551-565, 2004.

T. Deffieux et al., "Shear wave spectroscopy for in Vitro quantification of human soft tissues visco-elasticity," IEEE transactions on Medical Imaging, vol. 28, No. 3, Mar. 2009, pp. 313-322.

R. R. Bouchard et al., "Image quality, tissue heating, and frame rate trade-offs in acoustic radiation force impulse imaging," IEEE Transactions on Ultrasonics, Ferroelectrics and Frequency Control, vol. 56, No. 1, Jan. 2009, pp. 63-76.

J. Bercoff et al., "Supersonic Shear Imaging: A new technique for soft tissue elasticity mapping," IEEE Transactions on Ultrasonics, Ferroelectrics and Frequency Control, vol. 51, No. 4, Apr. 2004, pp. 396-409.

* cited by examiner

SPATIALLY-FINE SHEAR WAVE DISPERSION ULTRASOUND VIBROMETRY SAMPLING

This application claims the priority of international application number PCT/IB2010/052863, filed Jun. 23, 2010, which claims the benefit of U.S. provisional application Ser. No. 61/226,485, filed Jul. 17, 2009.

FIELD OF THE INVENTION

The present invention is directed to measuring a shear wave and, more particularly, to doing so by Shear Wave Dispersion Ultrasound Vibrometry (SDUV).

BACKGROUND OF THE INVENTION

Mechanical changes in living tissue correlate with pathological changes. As between healthy and pathological tissue, the shear elastic modulus (stiffness) and viscosity can vary significantly. With the advent of ultrasound elasticity imaging development over the past decade, many clinical studies have shown that tissue visco-elastic properties provide useful information to physicians for better cancer diagnosis and therapy assessment.

Shear Wave Dispersion Ultrasound Vibrometry (SDUV) is an acoustic radiation force based technique that measures tissue shear elasticity and viscosity by characterizing shear wave speed dispersion, i.e., by frequency. An application of this technique is the non-invasive measurement of liver stiffness to stage liver fibrosis and cirrhosis.

Interrogation by ultrasound, for purposes of medical imaging, often makes use of longitudinal waves. In body tissue, the ultrasound propagates in wave form. In effect, particles all along the propagation path vibrate, in place, back and forth, and the vibration occurs in the direction of propagation. The vibrations create compressions and rarefactions. These are modeled as the peaks and valleys of a sinusoid. Energy is conveyed to the target and back by means of the oscillatory particle movements.

An ultrasound shear (or transverse) wave, by contrast, is characterized by back and forth in-place movement that is perpendicular to the direction of propagation. Oscillation one way creates the peaks, and the other way creates the valleys.

Performing SDUV entails issuing a series of focused longitudinal-wave push pulses. They are high intensity, narrow bandwidth signals which are fired with a repetition rate of (say) 100 Hz. After several of these pulses are fired, each laterally coinciding and in the same direction, they establish a shear wave which propagates out from the focus and in a direction perpendicular to that of the push pulses. The focal depth has been selected so that the shear wave travels through a region of interest (ROI).

A longitudinal-wave tracking pulse is issued to the ROI to assess, at the sampling point, the amplitude of the shear wave. This measurement is used in estimating the phase of the shear wave at the sampled location.

To sample another location, another push pulse issues to the same pushing focus, followed by a tracking pulse to that location. This second cycle is needed, because the difference in phase between two points is used in the determining of elasticity and viscosity.

Shear waves with frequencies of typically 100 Hz and harmonics (200 Hz, 300 Hz, 400 Hz), i.e., components (or "monochromatic shear waves"), are present because the envelope of the pushing pulse is a square wave. The speed estimations at the different frequencies are used in deriving tissue shear elasticity and viscosity.

SUMMARY OF THE INVENTION

Shortcomings of the prior art of record are addressed hereinafter.

One main challenge associated with detecting radiation-force-induced shear waves using SDUV is the relatively low amplitude vibration. Axial displacement is on the order of 10 μm. The vibration amplitudes are therefore susceptible to noise. System electronic noise and patient motion such as cardiac or respiratory motion will contribute significant noise to shear wave displacement estimation.

In addition, fast imaging is required to detect the shear waves. Vibrations at up to 400 Hz must be recorded, because higher frequency shear waves are attenuated by the medium. Accordingly, to safely exceed the Nyquist threshold, each spatial location must be sampled at greater than 1000 Hz to prevent aliasing. Since the tracking pulse repetition frequency is limited by the speed of sound in tissue and the depth of the ROI, this limits the number of spatial locations that can be sampled, using conventional non-multiline detection sequences.

Using a multiline beamformer, as proposed hereinafter allows for finer spatial sampling of the displacement field, and/or spatial sampling in both the elevation and lateral imaging planes (when using 2D arrays vs. conventional 1D arrays). Since more information is extracted from each of the detection pulses, the robustness of the elasticity measures from SDUV is increased. As an added benefit, the total time spent in the procedure can therefore be shortened. This is advantageous from a patient convenience standpoint, and for reducing the potential impact of thermal effects from the repeated delivery of pushes to the excitation point. In addition, the increased pace of radiofrequency (RF) data acquisition makes way for the employment of other shear wave imaging/quantification techniques that require high spatial resolution with high speed.

In one version of the present invention, shear wave dispersion ultrasound vibrometry (SDUV) is performed by forming, from a single tracking pulse, in-parallel-directed receive lines for making measurements of a monochromatic shear wave.

As an aspect, from at least one other tracking pulse, the forming is executed so as to overlap resulting receive lines to increase depth of field.

More particularly, in some embodiments, the increasing entails combining from among the overlapped receive lines to create at least one reconstructed A-line.

Related other possible aspects involve forming, from differently-timed ones of the at least one other tracking pulse, respective pluralities of reconstructed A-lines created by the combining.

As a specific embodiment, making measurements includes making amplitude measurements of the monochromatic shear wave.

What is proposed herein is implementable as an apparatus for performing shear wave dispersion ultrasound vibrometry (SDUV), configured for forming, from a single tracking pulse, a plurality of in-parallel-directed receive lines for making measurements of the monochromatic shear wave.

Such apparatus may be characterized in that the tracking pulse, and at least one laterally-offset tracking pulse, are focused to a common depth, the apparatus being configured for, based on echo data from the pulses focused to that depth, reconstructing a shallower transmit focus.

Or, in an alternative or supplemental aspect, the apparatus is configured for such forming for at least one other tracking pulse and so as to overlap receive lines, and further configured for interpolating pulse firing times, to, in determining phase difference, correct for intersample wave propagation.

In one form, a computer software product for performing shear wave dispersion ultrasound vibrometry (SDUV) includes a computer readable medium embodying a computer program that includes instructions executable by a processor to form, from a single tracking pulse, in-parallel-directed receive lines for making measurements of a monochromatic shear wave.

Further, in some versions, performing shear wave dispersion ultrasound vibrometry (SDUV) comprises, over a plurality of locations by means of a plurality of passes over the locations, sampling in an interlaced pattern for making measurements of a monochromatic shear wave.

In a specific variant of these versions, the locations sampled in one from among the plural passes interleave with locations sampled in a next one from among said plural passes.

As a possible aspect, results of the sampling at a given one of the locations over multiple passes are compared to a reference A-line to determine displacement of the monochromatic shear wave at that location.

Analogously, in some aspects a device for performing shear wave dispersion ultrasound vibrometry (SDUV) is configured for, over a plurality of locations by means of a plurality of passes over the locations, sampling in an interlaced pattern for making measurements of a monochromatic shear wave.

What is proposed herein likewise can take the form of a method for performing shear wave dispersion ultrasound vibrometry (SDUV), which includes making measurements of a monochromatic shear wave and applying, to the measurements, a bank of filters that are tuned to respective candidate speeds of the wave, without the need to determine a difference between phases of the wave at different spatial locations.

In a further aspect, a low-pass filter may be used on the measurements, to reduce noise in preparation for the applying.

In yet another aspect, the filters in the bank are two-dimensional, one dimension being spatial location and the other dimension being time.

In an additional aspect, a device for performing shear wave dispersion ultrasound vibrometry (SDUV) is configured for making measurements of a monochromatic shear wave and applying, to the measurements, a bank of filters that are tuned to respective candidate speeds of the wave, all without the need to determine a difference between phases of the wave at different spatial locations.

As further, additional aspects, apparatus and devices described above may be implemented as one or more integrated circuits.

Details of the novel, fine-spatial-sampling methodology for SDUV are set forth further below, with the aid of the following drawings.

DETAILED DESCRIPTION OF EMBODIMENTS

Figure 4:
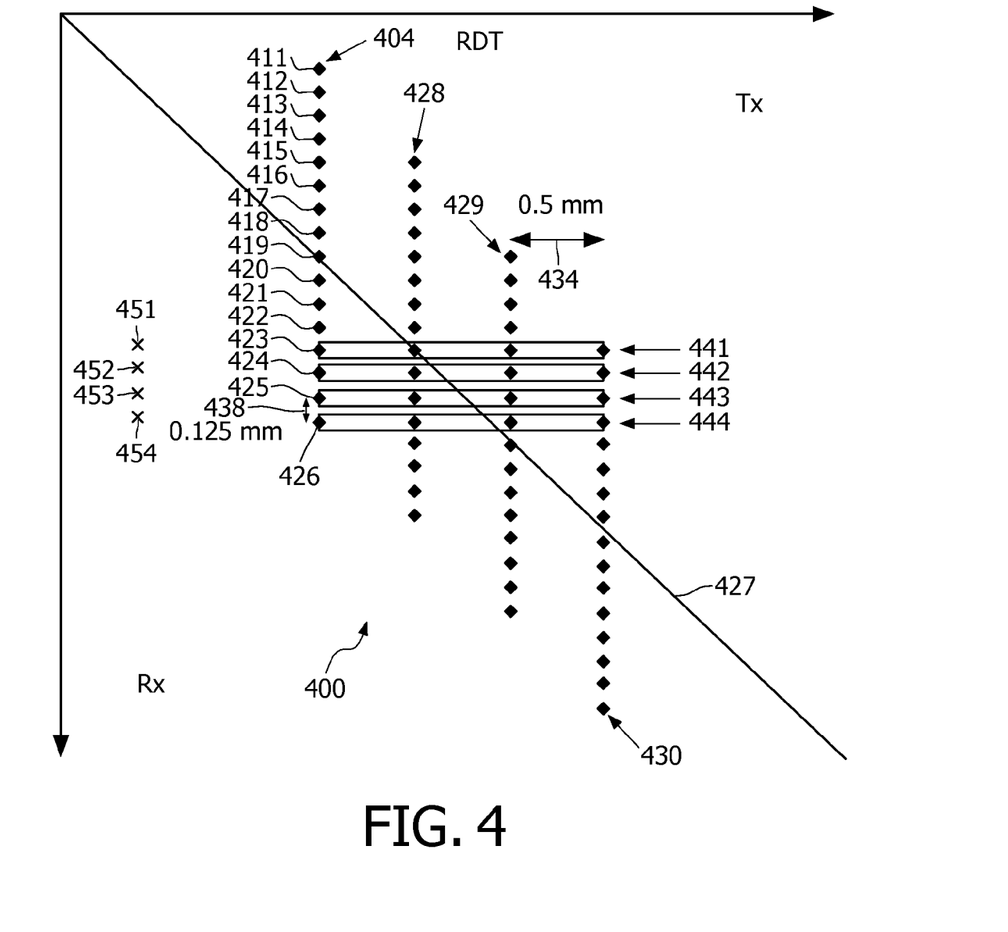
FIG. 4 is a schematic, transmit-receive diagram illustrating, by example, SDUV sample acquisition using retrospective dynamic transmit (RDT) as implemented on a 16× multiline beamformer.

A general discussion is first had of one version of SDUV with faster sampling. What follows, in this context and starting with FIG. 4, is further exemplary development related to finer spatial sampling.

Figure 1:
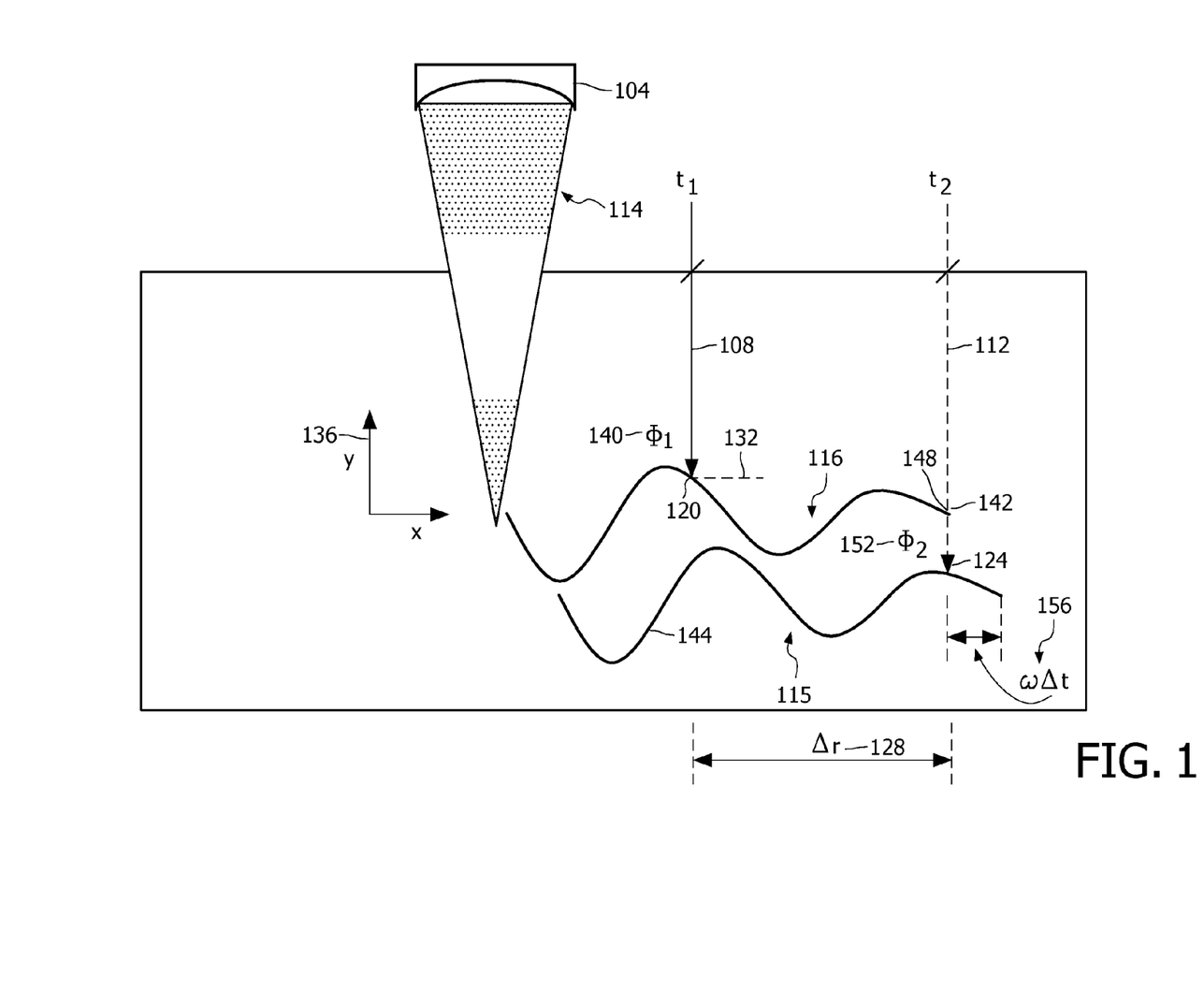
FIG. 1 is a schematic diagram exemplary of two consecutive SDUV samples.

FIG. 1 depicts, by way of illustrative and non-limitative example, a relation between two consecutive SDUV samples. An ultrasound pushing probe 104 is shown, along with first and second tracking pulses 108, 112 issued at respective sampling times t1, t2, by an ultrasound tracking probe (not shown). The pushing probe 104 sends out a series of focused pushing pulses (or "pushes") 114 to establish a shear wave 115, a frequency component of which (or "monochromatic shear wave") is represented by a first trace 116. Tissue vibrates along the y-direction and the shear wave 115 propagates along the x-direction.

Two separate probes can be used for pushing and tracking respectively. However, this type of bulky configuration is not practical for clinical applications.

In addition, in the case of separate single-element transducers, it requires repeated firing of the push pulses in order to measure the shear wave phase delay at different lateral positions, resulting in repeated tissue heating.

If, on the other hand, tracking is implemented with an array transducer, the need for repeated pushes is alleviated in accordance with the proposal herein.

Moreover, one single array transducer can serve both functions of pushing and tracking. A dual-purpose single array transducer would make the system more compact and easier to control. However this configuration needs more hardware and software support to ensure it is feasible to generate acoustic radiation force and image the resulting shear wave 115 by a single transducer. The single transducer can be a single-row array (1D transducer) or multiple-row array (1.75 or 2D transducer) that allows for lateral and elevation push and/or tracking pulse locations.

Advanced 2D array technology will allow tracking pulses to be sent in 3D dimensions; however, the following discussion relates to tracking tissue motion in the axial-lateral plane. The same treatment applies to the axial-elevation plane, without loss of generality.

The tracking pulses 108, 112 are targeted to respective locations 120, 124 spatially separated by an inter-location distance 128 of Δr. The distance 128 is typically in the millimeter range, because the shear wave 115 attenuates with propagation distance. An amplitude (or displacement) 132, as represented on the y-axis 136, is measured. Based on the amplitude 132, a phase 140 of $\Phi_1$ at the location 120 can be derived, provided the Nyquist threshold is met regarding sampling frequency. The Nyquist threshold can be met by sufficient frame rate, i.e., multiple sampling passes over the location 120 with sufficient frequency.

Figure 2:
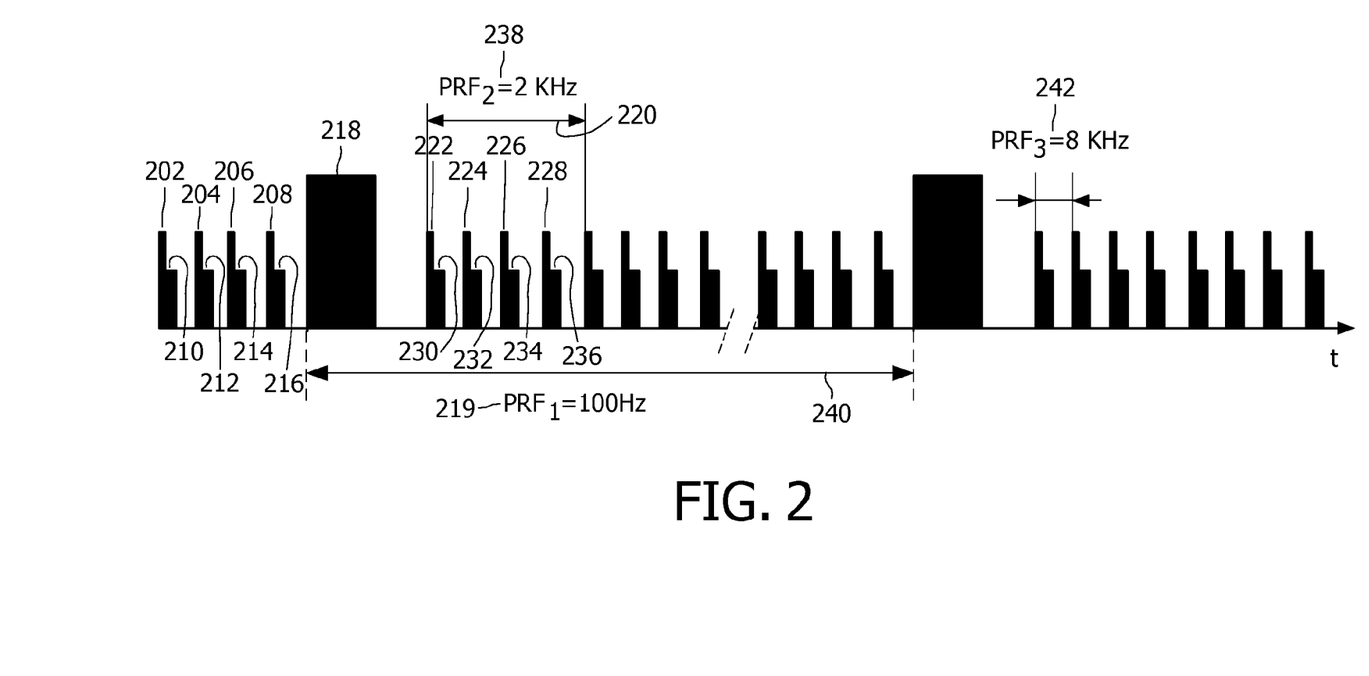
FIG. 2 is a timeline of an example representative of sequential SDUV tracking.

FIG. 2 depicts one example of sequential SDUV tracking. Before any push pulses 114 vibrate the region of interest (ROI), reference tracking pulses 202, 204, 206, 208 issue, targeted to respective sampling locations $x_1, x_2, x_3, x_4$. The locations $x_1, x_2, x_3, x_4$ are aligned radially out from a point $x_0$, i.e., in a propagation direction of the shear wave 115 to be created by the push pulses. The reference tracking pulses 202, 204, 206, 208 are each followed respectively by their echoes 210, 212, 214, 216. Then, the shear wave 115 is established at a location $x_0$, i.e., the site of the excitation point. This is done by an initial series (not shown in FIG. 2) of push pulses 218 that are fired at a push frequency 219 which might typically be approximately 100 Hz. A tracking-sequence-initiating onset of the push pulses 218 can issue once the wave 115 has been established. A pass 220 of tracking pulses 222, 224, 226, 228 follows, steered, serially, pulse-by-pulse. The tracking pulses 222, 224, 226, 228 are targeted to the respective sampling locations $x_1, x_2, x_3, x_4$. Each of the pulses 222, 224, 226, 228 is followed by its respective echo 230, 232, 234, 236, from which the respective receive A-line is then beamformed. The pass 220 issues at a same-location tracking frequency 238 of 2 KHz. Accordingly, 20 passes (i.e., "frames") 220 can follow the push 218. Also, the same-location tracking frequency 238 of 2 kHz allows phase measurement of components 116 of frequencies of up to about 1 kHz, the Nyquist threshold. Each of the tracking pulses 222, 224, 226, 228 can serve to simultaneously provide measurement of each of the frequency components, within the inherent limits of the Nyquist threshold.

Regular B-mode imaging is utilized, i.e., the tracking pulses 222, 224, 226, 228 are electronically focused and steered back and forth laterally at different locations $x_1, x_2, x_3, x_4$ between two adjacent pushing pulses 218. Receive A-lines at different locations $x_1, x_2, x_3, x_4$ are therefore formed sequentially.

The number of transmission lines within each B-mode frame should be limited so that the sampling PRF (pulse repetition frequency) for the shear wave 115 is high enough. As seen in FIG. 2, for example, for each location $x_1, x_2, x_3, x_4$, the same-location tracking frequency 238 is 2 KHz ($PRF_2$), while the transmission A-line frequency 242 is 8 KHz ($PRF_3$). This is merely illustrative. If the highest harmonic measured is 400 Hz, this indicates that the detection pulses (laterally identically in a given direction) should be fired at a minimum rate of say 1000 Hz (allowing a small margin over Nyquist). In this case, $PRF_2$ would be set to 1 kHz. Therefore it will be possible to transmit beams to 8 kHz/1 kHz=8 locations.

Merely a single push/tracking sequence 240 is needed to obtain all of the SDUV information needed for shear wave speed estimation. Faster data acquisition is a key requirement to advance the technique of SDUV from a single-point "virtual biopsy" tool to a possible real-time imaging modality. Notably too, the heat generated in the tissue and transducer can be decreased while maintaining the number of lateral locations $x_1, x_2, x_3, x_4 \ldots$ observed for shear wave tracking. The faster data acquisition can also further reduce noise in shear wave displacement estimation, especially therefore avoiding large temporal-scale noise such as respiratory motion that tissue might otherwise experience over the course of different push/tracking sequences 240.

Figure 3:
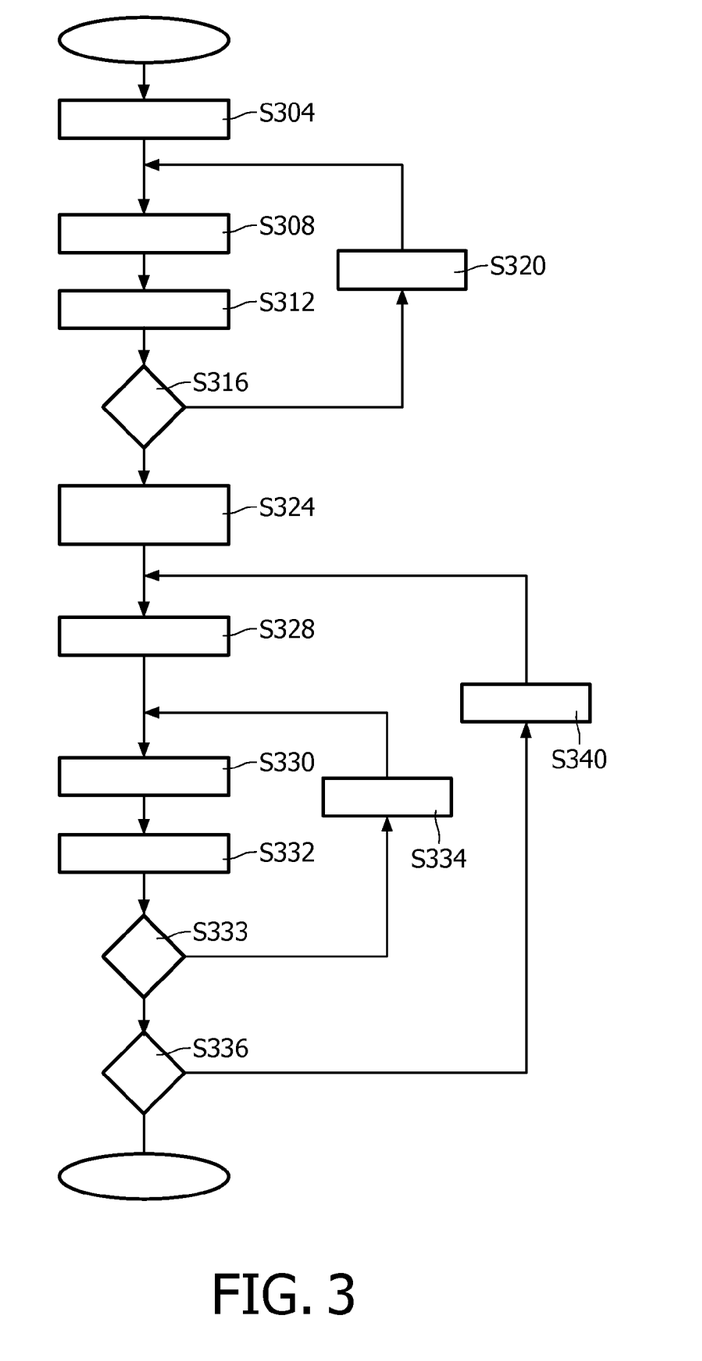
FIG. 3 is a flow chart corresponding to the timeline of FIG. 2.

FIG. 3 is a flow chart corresponding to the timeline of FIG. 2. Focus is set to the first location $x_1$ (step S304). A current tracking reference pulse 202 is emitted (step S308). Its echo 210 follows (step S312). If there are more locations (i.e., $x_2, x_3, x_4$) to be measured (step S316), the focus is steered to the next location (step S320), and processing returns to the tracking reference pulse emitting step S308 with that next location as the current location. On the other hand, if there are no further locations to be measured (step S316), the push pulse 218 is fired successively to establish the shear wave 115 (step S324). The focus is then set to the first location $x_1$ (step S328). The current tracking pulse 222 is emitted (step S330), and its echo 230 returns (step S332). If there are more tracking pulses (i.e., 224, 226, 228) to issue in the current pass 220 (step S333), the focus is set to the corresponding next location (step S334) and processing returns to the tracking pulse emitting step S330 with the next location as the current location. Otherwise, if there is no next tracking pulse to be emitted, query is made as to whether another pass is to be made over the locations $x_1, x_2, x_3, x_4$ (step S336). If a next pass is to be made, that next pass is made the current pass (step S340), and processing returns to the beginning of the next pass 220 at the step S328. If, however, there is no next pass 220 to be made (in the current push/tracking sequence 240), sampling is completed. A single push/tracking sequence 240 suffices, in the instant proposed technique, to provide all of the sampling needed for SDUV determination of shear wave speed and, in practical embodiments, for calculation of tissue elasticity and viscosity.

FIG. 4 represents one example of an SDUV sample acquisition scheme 400 using retrospective dynamic transmit (RDT), as implemented on a 16× multiline beamformer, i.e., a beamformer that forms 16 receive lines from one transmit beam (or "transmit" for short).

With a multiline beamformer, SDUV sampling will still be sequential, but by group of spatial locations. To each group, a transmission beam is issued. If the ROI is located at a different depth than the focus of the transmission beam, then the transmission beam will be broader than at the focus and will insonify the group of spatial locations. Alternatively, the beam can be weakly focused at the same depth as the ROI, with a breadth that is sufficient to insonify the group of spatial locations.

From the echoes of a transmission beam created from a single tracking pulse 404, 16× beamforming circuitry forms 16 in-parallel-directed receive lines 411-426 for making measurements of the monochromatic shear wave 116. As indicated by a diagonal, sub-aperture tracking line 427, the first eight receive lines 411-418 are on one side of the center of the transmit, and the second eight receive lines 419-426 are on the other side.

Other tracking pulses 428, 429, 430, and the first tracking pulse 404, are all differently-timed. If the transmission A-line (or "tracking pulse") PRF 242 is set equal to 10 kHz for example, the single tracking pulse 404 issues 100 µs before the next tracking pulse 428. 100 µs later, the next pulse 429 fires, and so on.

Each of the tracking pulses 404, 428, 429, 430 is formed by a respective then-currently active sub-aperture of the tracking probe. The active sub-aperture is a subset of the transducer elements that are currently active to transmit ultrasound. Thus, for example, after the tracking pulse 404 fires, the currently active sub-aperture shifts (e.g., one or more elements on one side of the aperture are excluded and one or more elements on the other side are included). When the next tracking pulse 428 then fires, it occurs from the shifted sub-aperture. The spatial distance between adjacent apertures is referred to hereinafter as a transmit spacing 434, which, in the current example, is 0.5 mm. The focal point of the tracking pulse also shifts by the transmit spacing 434 between consecutive tracking pulses.

The 16 in-parallel-directed receive lines 411-426 (i.e., dynamically-formed receive lines that are spatially parallel) are formed from the echo data received after the transmit 404.

Each of the receive lines 411-426 is formed by a receive sub-aperture. The receive sub-aperture is a subset of the transducer elements that contribute to a given receive line.

The spatial distance between the receive lines 411-426 is referred to hereinafter as a receive spacing 438. In this example, it is 0.125 mm, or one quarter of the 0.5 mm transmit spacing 434.

Making the receive spacing 438 a fraction of the transmit spacing 434 allows for more dense sampling, as will be discussed in more detail below.

All of the acquired echo radiofrequency data is saved in temporary storage. Retention of acquired data will continue as the sub-aperture shifts and eventually assumes its final position in the transducer array, i.e., so that an entire pass of data is acquired. In addition, data will be retained pass-to-pass.

Due to the shift in sub-aperture between the firing of the first tracking pulse 404 and the next tracking pulse 428, the last twelve receive lines 415-426 of that first pulse spatially overlap, respectively, with the first twelve receive lines of that next pulse. Likewise, due to the sub-aperture shift with each succeeding tracking pulse, the last twelve receive lines of the tracking pulse 428 overlap with the first twelve receive lines of the next tracking pulse 429, and so on.

By the time the fourth tracking pulse 430 fires, respective receive lines of all four tracking pulses 404, 428, 429, 430 overlap and can be combined to form four reconstructed A-lines 441-444.

The first reconstructed A-line 441, for example, is formed from the first receive line 423, combined with the three respective receive lines of the immediately-subsequent tracking pulses 428-430. The combining occurs in accordance with retrospective dynamic transmit (RDT). The effect of RDT focusing can be analyzed using the virtual transducer approximation proposed by Passman and Ermert in 1996. See C. Passmann & H. Ermert, "A 100-MHz ultrasound imaging system for dermatologic and ophthalmologic diagnostics," IEEE Trans. Ultrasonics, Ferroelectrics and Frequency Control, vol. 43, no. 4, pp. 545-52 (1996). This technique is further discussed in commonly-assigned U.S. Patent Publication Number 2009/0069693 to Burcher et al., entitled "Retrospective Dynamic Transmit Focusing for Spatial Compounding," (hereinafter "the '693 publication"). The disclosures of both publications are hereby incorporated herein by reference in their entirety.

The first reconstructed A-line 441 is for measuring the shear wave 115 at a spatial location 451. Likewise, the immediately-subsequent reconstructed A-lines 442-444, which are laterally offset from the first reconstructed A-line 441, are for measuring the shear wave 115 at respective spatial locations 452-454.

Although here four receive lines are combinable per reconstructed A-line, fewer receive lines can be combined. The number that are actually combined depends on the depth of the ROI and its consequent insonification coverage by tracking pulse. Also, the instant example is not limitative. Thus, the aperture shift may be to an extent that more or fewer receive lines are combinable to form a reconstructed A-line.

By virtue of the combining, depth of field (DOF), the region over which the transmit is well-focused, and signal-to-noise ratio (SNR) are increased. In comparing the reconstructed A-line 441 to any of the receive A-lines from which it is reconstructed, the length over which its spatial resolution is useful has been increased by the greater DOF afforded by RDT.

A-line reconstruction based on potentially four receive lines begins with the first four reconstructed A-lines 441-444, and proceeds with each new tracking pulse. Thus, the next tracking pulse allows for the formation of four new reconstructed A-lines at respective spatial locations. Likewise, for the rest of the frame, each succeeding tracking pulse leads to the formation of a respective plurality of reconstructed A-lines, that plurality being, in the current example, made up of four reconstructed A-lines.

The shear wave 115 is therefore finely sampled, without a reduction in the pace by which tracking pulses issue.

It is noted that non-RDT embodiments are possible, where they receive focal locations are not staggered overlapping but merely adjoin one another. The shear wave 115 is still finely sampled without a reduction in the pace of tracking pulse issuance. The number of in-parallel-directed receive lines per tracking pulse may be four, for example—two on one side of the tracking beam and two on the other side.

Figure 5:
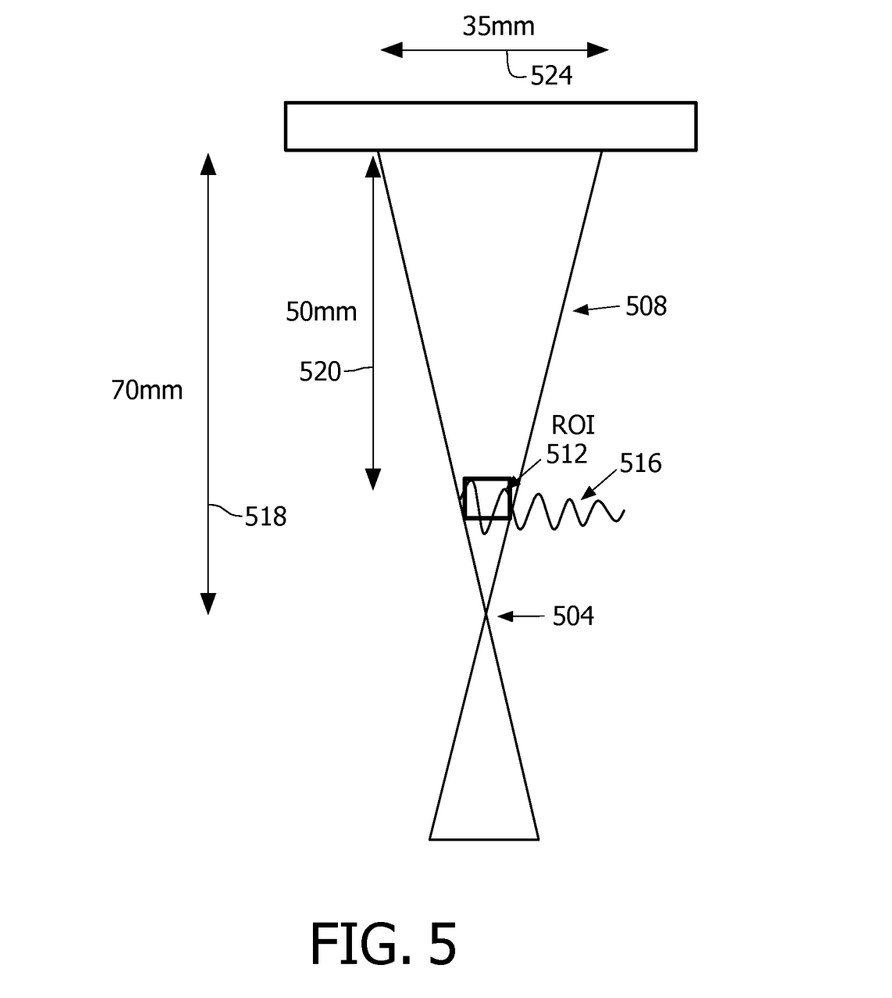
FIG. 5 is a schematic diagram demonstrating, in an RDT context, a possible placement of a detection beam transmit focus.

FIG. 5 demonstrates, in an RDT context, a possible placement of a focus 504 of a detection beam 508 formed by the tracking pulse 404. A region of interest (ROI) 512, as indicated by the square outline, is where a shear wave 516 is present. In order to ensure that insonification by the detection beam 508 spans the locations to be sampled by means of the receive lines to be acquired, it would be advantageous to place the focus 504 deep to the ROI 512. A physical focus position shown in FIG. 5 is at 70 mm, a common depth 518 for transmits insonifying a given point in the ROI and therefore to be RDT-combined. Although the detection beam 508 is wide at the depth 520 of the ROI 512, the RDT reconstructed detection beam will, at that depth, be narrow—having the same width as at the (physical) focus 504. In effect and by way of example, from among the temporally-initial tracking pulse 404, and at least one laterally-offset tracking pulse 428-430 forming a transmit to be RDT-combined with that of the temporally-initial tracking pulse, at least some are focused to a common depth 518. A shallower transmit focus, to the depth 520, is reconstructed based on echo data from those of the pulses 404, 428, 429, 430 focused to the common depth 518.

This also allows the use of a larger transmit aperture 524, which may increase the total power that can be transmitted in the detection beam 508. More power affords greater sensitivity to the minute wave amplitude displacements 132, on the order of about 10 μm.

Alternatively, the focus 504 of the detection beam 508 may be placed shallow to the ROI 512.

There are additional considerations when applying RDT to SDUV.

Firstly, RDT assumes that the tissue does not move between transmit events. If displacement does occur, then it will reduce the coherence between the combined transmits and lead to signal cancellation. This would therefore appear to be incompatible with SDUV, since the tissue is being displaced by the shear wave. However, in practice the displacements 132 are of such small magnitude (typically <10 μm) that this is a small fraction of the wavelength of the tracking pulse (e.g. 300 μm at 5 MHz). Therefore, the shear wave displacements 132 will not cause any significant loss in coherence during the transmit reconstruction.

Secondly, even with non-multiline sequences 220, because the beams at different lateral locations $x_1$, $x_2$, $x_3$, $x_4$ are fired consecutively, the displacement estimates at different lateral locations are sampled at different times t1, t2 . . . .

With reference back to FIG. 1, and, assuming for example a non-multiline sequence, for simplicity of demonstration, if the sampling times t1, t2 were simultaneous, return data, i.e., echo data, from the tracking pulse 112 would have suggested a phase 142 corresponding to sampled point 148 on the first waveform 116.

However, the sampling times t1, t2 are not simultaneous if tracking pulses are sequentially fired for these two locations 120, 124. (Likewise, a reconstructed A-line subsequent, in the frame, to the reconstructed A-line 444 would be a sample of the wave 115 at a different time.)

In fact, by the time $t_2$, the shear wave component 116 has propagated forward, as a waveform having a frequency component represented by a second trace 144.

The corresponding sampled phase 152 of $\Phi_2$, on the second trace 144, differs from the phase 140 of $\Phi_1$, on the first trace 116, by a phase difference of $\Delta\Phi=\Phi_2\Phi_1$.

As seen from FIG. 1, $\Delta\Phi$ is less than the difference between the phases 140, 142 that simultaneous tracking pulses would have fetched.

As further seen from FIG. 1, $\Delta\Phi$ is smaller by an intersample-delay-based phase correction 156 of $\omega\Delta t$, "$\omega$" representing the angular frequency of the monochromatic shear wave 116, with "$\Delta t$" signifying the delay between the taking, at the respective sampling times t1, t2, of the two samples.

Yet it is the difference between the phases 140, 142 that, along with $\omega$ and $\Delta r$, define the propagation speed of the shear wave frequency component 116.

That difference is calculated by adding, to the phase difference $\Delta\Phi$, the intersample-delay-based phase correction 156 of $\omega\Delta t$.

The speed of the monochromatic shear wave 116 is given by the following formula:

$$c_s(\omega) = \frac{\omega \Delta r}{\Delta\phi + \omega\Delta t} \quad \text{(formula 1)}$$

A derivation of the formula 1 is as follows:

$c_s(\omega)=\lambda f$, where $c_s$ is propagation speed, $\lambda$ is the wavelength, "$\omega$" represents the angular frequency of the monochromatic shear wave 116 and f is the wave's frequency.

Also, $\omega=2\pi f$, and $\Delta r=\lambda\Delta\Phi/2\pi$, where $\Delta\Phi$ represents the phase difference, for a given moment, between the two samples taken simultaneously.

All parameters are assumed to be positive.

Substituting values yields $$c_s(\omega) = \frac{\omega \Delta r}{\Delta\phi}$$

To account for the intersample delay between the two differently-timed samples taken at the times t1, t2, the intersample-delay-based phase correction 156 of $\omega\Delta t$ is added to $\Delta\Phi$ to arrive at formula (1), as explained above in connection with FIG. 1.

The same phenomenon occurs with an RDT sequence, and must be taken into account when extracting amplitude information based on A-lines directed differently and acquired at different times, e.g., the reconstructed A-line 444 and a reconstructed A-line later acquired in the frame.

To account for this in the application of formula 1, when RDT combines transmits to interpolate intermediate transmit locations (as disclosed in the '693 publication), the sampling time (as well as the sampling location) is interpolated between transmits. In other words, in the case of pulse firing times, and in the case of the transmit locations upon firing (e.g., those along the sub-aperture tracking line 427 for transmits used in the reconstruction), they are interpolated by the same RDT interpolation weightings. Thus, $\Delta t$ and $\Delta r$ can be computed for substitution into formula (1).

It is noted that formula (1) assumes tracking, i.e., the emission of tracking pulses, in the (radial) outward direction of shear wave propagation. If tracking is performed in the reverse direction, the "+" sign in the denominator becomes a "−" sign. By analogous reasoning, if the tracking direction alternates with passes 220, the $\Delta\Phi$ calculation for a pair of spatial locations 120, 124 can be averaged with the same calculation made based on an adjoining pass, so that the denominator is simply $\Delta\Phi_{avg}$.

Formula (1) also assumes the two differently-located samples were acquired at different times.

In the non-RDT, non-multiline example illustrated in FIGS. 2 and 3, differently-located samples are acquired at different times.

In a non-RDT, multiline embodiment, the receive lines of a given transmit are not differently timed. So, the intersample-delay-based phase correction 156 of $\omega\Delta t$ is omitted from the denominator of formula (1) for those speed calculations, if any, based on receive lines of a given transmit. However, formula (1) is otherwise used, as is.

In an RDT context, a reconstructed A-line subsequent, in the frame, to the reconstructed A-line 444 would be a sample of the wave 115 at a different time. Likewise, the reconstructed A-lines 441-444 will generally have different sampling times, the latter being based on the respective interpolations of transmit firing times. Those respective interpolations each use different interpolation weights which are proportional to the transmit field strength at the target location along the A-line to be reconstructed. Typically, then, the first reconstructed A-line 441 will have an earlier sampling time than the immediately-subsequent reconstructed A-line 442 for purposes of the speed calculation. So, formula (1) is applicable as is.

Figure 6:
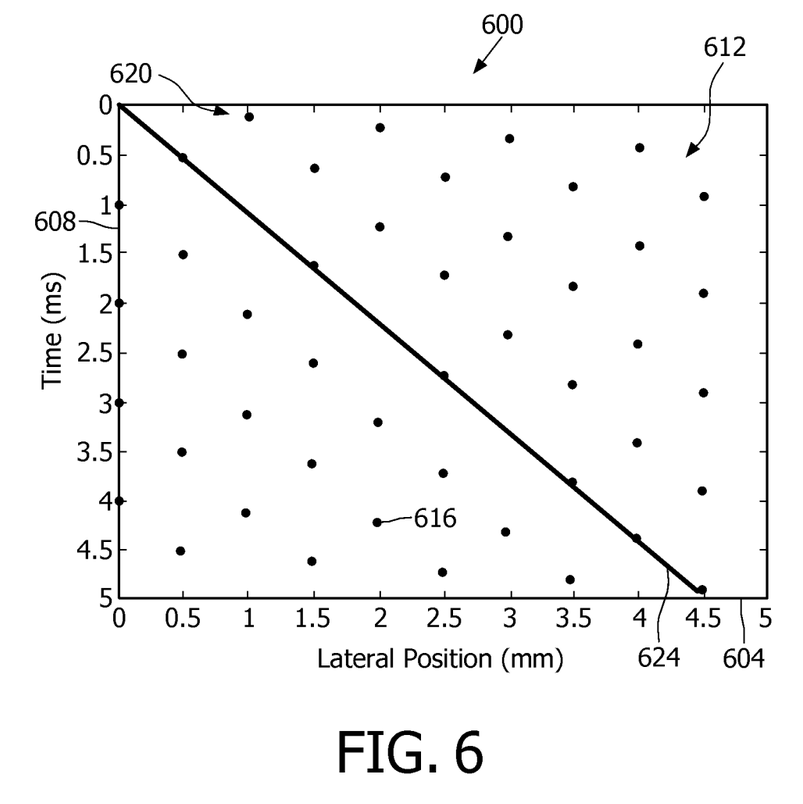
FIG. 6 is a graphical rendition of an exemplary interlaced sampling scheme.

FIG. 6 exemplifies an interlaced sampling scheme 600. It does not rely on a multiline beamformer or RDT. For simplicity it will therefore be described for a basic beamformer capable of forming only a single receive line per tracking pulse 222. The x-axis 604 is lateral position, in millimeters, from the first sampling location x1. The y-axis 608 is the time transpired since the first tracking pulse 222. A motion field 612 of measured displacements 616, whose magnitudes are not shown, is represented. The observations 616 are indicated for several sampling passes over the sampling locations x1, x2, x3, x4 . . . .

The present inventors have observed that it would be desirable to create a sample scheme in which samples that ordinarily match an appropriately-spaced-apart pattern, (e.g., $1^{st}$, $4^{th}$, $7^{th}$, $10^{th}$ . . . ), "ride" the propagation wave phase-wise in-place, or approximately so. Each of the respective displacements 616 would, accordingly, be nearly the same, thereby reducing sampling artefacts. Such a device is particularly beneficial when faced with tight PRF and other implementation constraints.

As previously noted, the rate of temporal sampling is limited by the maximum frequency of the shear waves. To sample a 400 Hz shear wave well requires a temporal sampling rate of at least 1000 Hz. In turn, the total sampling rate (over all locations) is bound by the maximum PRF 242 permitted by the imaging depth. The maximum PRF 242 may be, as mentioned above in connection with an example, 10 kHz, which dictates that at most 10 spatial locations can be sampled without risking the emergence of sampling artefacts such as aliasing.

To summarize, it is desirable to sample many lateral locations $x_1, x_2, x_3, x_4$ to increase the number of measurements for robustness. The number of lateral positions is limited by the maximum PRF 242 as noted just above, although the PRF should be large enough to allow for enough locations to be sampled without sampling artefacts.

It is also of benefit that the lateral locations be as close to the excitation point $x_0$ as possible to avoid attenuation of the shear wave amplitude which makes it hard to measure the amplitude, although the first lateral location $x_1$ is limited in its closeness to the excitation point, due to near-field effects. The closeness between locations $x_i$, $x_{i+1}$ is constrained, however, by other engineering considerations.

The interlaced sampling scheme 600, in which sampling in one pass is location-wise interleaved with sampling in the next pass, takes advantage, firstly, of the fact that the motion field to be measured is highly structured: it consists of shear waves 116 with a limited range of speeds.

Secondly, the nature of the two axes 604, 608, relating to position and time, respectively, is such that sampling consecutive locations $x_i, x_{i+1}, x_{i+2}$ . . . implies a constant tracking-pulse translation speed. This is seen in FIG. 6 from the first row 620 of observations. Since they imply a line of constant slope, a constant tracking-pulse translation speed is implicit. In this context and with regard to the constant tracking-pulse "translation," if the beam is steered in a non-parallel manner, the "translation" can be considered to occur between lateral locations $x_i, x_{i+1}$.

However, the above design criteria call for a higher translation speed than any of the monochromatic wave speeds $c_s$.

A slower, constant tracking-pulse translation speed is, nevertheless, discernible by confining scrutiny to the sampling of two consecutive locations $x_i, x_{i+1}$ by means of separate passes 220. This is exemplified by the slanted line 624, characterized in that samples of interest at the two locations $x_i, x_{i+1}$ are in consecutive passes 220.

The same phenomenon of higher- and slower-speed patterns exists for a non-interlaced motion field, i.e., a field in which in each pass 220 consecutive locations $x_i, x_{i+1}$ are sampled without skipping locations However, interlacing the sampling is a tool by which to craft more different constant tracking-pulse translation speeds, thereby increasing the potential to achieve a match (or near match as seen from the line 624) with the speed of the targeted shear wave 116. The need for such a technique arises because of the difficulty in otherwise manipulating parameters to alter the translation speed, given the above-discussed design constraints. Notably, too, interlacing the sampling results in the same number of samples. Also, it does not adversely impact the tracking pulse PRF 242, which remains constant.

As seen from FIG. 6, the motion field 612 is segmentable into observation lines parallel to the central, slanted line 624.

The consequent reduction of sampling artefacts can serve to mitigate any potential side effects of finer spatial sampling.

Figure 7:
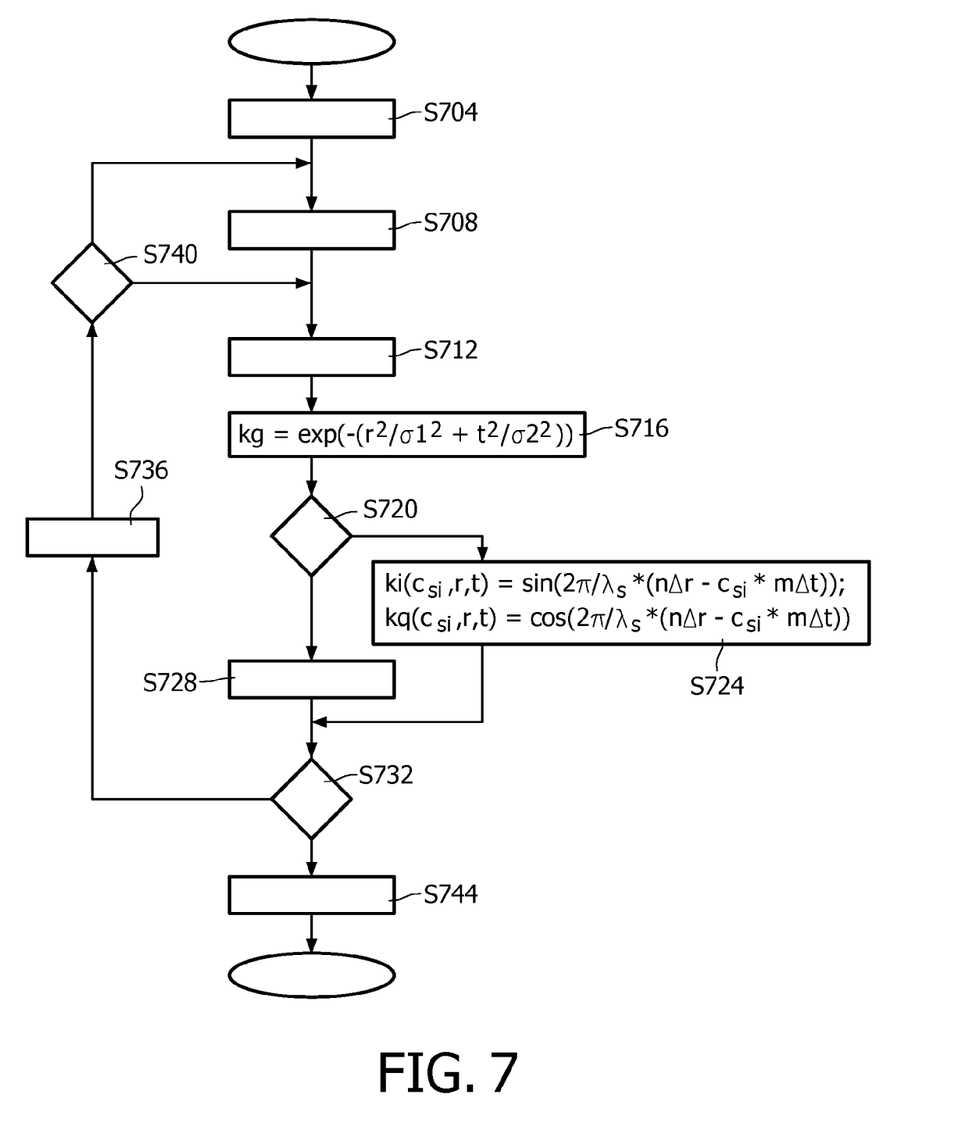
FIG. 7 is a flow chart representative of particular embodiments as examples of how to determine tissue shear elasticity and viscosity.

FIG. 7 shows particular embodiments as examples of how to determine tissue shear elasticity and viscosity. A first component 116, e.g., the fundamental, of a shear wave 115 is selected as the current component (step S704).

Echo RF data, which, in the RDT context, consists of the temporally-initial reconstructed A-lines 441-444, the ones subsequent in the frame, and ones in other frames, are acquired, in accordance with the multiline sample acquisition scheme 400 for example (step S708). For each of the spatial locations 451-454 . . . , the reconstructed A-lines at that location are each compared to the corresponding reconstructed reference A-line to determine the displacement 132 of the current wave component 116 at that location. A number of known approaches, such as cross-correlation or Doppler approaches can be used to calculate the displacements 132.

Likewise, in non-RDT, multiline and non-multiline contexts, same-located samples are compared (step S712).

Because of the finer sampling in accordance with the methods proposed herein, application is made, optionally, in some embodiments, of a low-pass filter (LPF) to the measurements 132 to reduce noise in the measurements. The LPF can be a two-dimensional filter for acting in the location and time dimensions 604, 608. An example of such a filter would be an anisotropic filter, such as a Gaussian kernel:

$$kg = \exp(-(r^2/\sigma_1^2 + t^2/\sigma_2^2)), \qquad \text{formula (2)}$$

where "r" represents location, "t" represents time, and $\sigma_1$ and $\sigma_2$ control the size of the filter in the spatial and temporal dimensions respectively.

If the motion field 612 consists of a single shear wave 116, then a contour on the motion field with constant displacement (i.e., since the interlaced scheme 600 is arranged, by appropriate intersample spacings on the axes 604, 608, to result in the slanted line 624 of essentially constant displacements 616) is a straight line which slopes, down and to the right, and whose slope or "gradient" is determined by the speed of the shear wave 116.

The motion field 612 can be represented by a two-dimensional matrix of displacements 616, one dimension being location and the other being time. Similarly, the expression on the right side of formula (1) is evaluated to create another two-dimensional matrix, the two matrices being convolved to reduce noise in the measurements 616.

An alternative filter is a steered filter:

$$ks = \exp(-(u^2/\sigma_3^2 + v^2/\sigma_4^2)), \qquad \text{formula (3)}$$

$$u = r + cs \times t$$

$$v = r - cs \times t$$

where cs is the angle of the filter (which represents a speed), "u" is in a direction aligned with the contours of waves propagating forward with a speed cs, and "v" is in a reverse direction aligned with the contours of hypothetical waves that could be imagined to be propagating backward, i.e., toward the excitation point $x_0$, with a speed cs. Sizing parameters $\sigma_3, \sigma_4$ control the size of the filter in the two directions, u and v. Typically, $\sigma_3$ will be larger than $\sigma_4$, so that more smoothing is applied in the v direction than the u direction.

If the motion field 612 consists of a single shear wave 116 propagating forward with speed cs, then lines of constant v will lie along contours on the motion field with constant displacement. The filter kernel ks in formula (3) will be aligned with the motion field 612. The angle of the filter is, in this context, given by the a priori speed of the shear wave 116. Optionally, the filter angle can be adjusted iteratively using the current estimate of the shear wave speed.

Convolving the kernel ks with the measurements 132 will smooth more in the parallel direction to the contour than in the perpendicular direction. Therefore for a given amount of noise reduction, it will tend to preserve the structure of the motion field 612 better than an isotropic filter (step S716).

An alternative to determining a difference between phases of the shear wave 116 at different spatial locations $x_i, x_j$, as in accordance with formula (1), is to apply a bank of two-dimensional filters, each tuned to a specific candidate wave speed.

If the filter bank is to be applied (step S720), a number of filters are used, covering the expected range of wave speeds. The motion field 612 is convolved with each of the filters (in turn, or in parallel). The filter with the largest output is taken as the best estimate of wave speed. The process can be iterated, making the estimate more accurate by tuning the filters to a more closely spaced selection of wave speeds, around the current estimate.

As an example, a motion field is represented in the form:

$$d(r,t)=d(n\Delta r, m\Delta t) \quad \text{formula (4)}$$

where "r" is the lateral position, "t" is the acquisition time, and "n" and "m" are sample indices, $\Delta r$ is the lateral sampling interval and $\Delta t$ is the time between displacement samples at the same lateral position.

The motion field in this example features, for simplicity of demonstration, a regular, evenly-spaced grid, in which initial values of "t" (like "r") are implicitly initially zero. This, then, corresponds to sampling in a non-interlaced pattern, rather than in the interlaced sampling scheme 600. However, this example can be adapted to the interlaced sampling scheme by appropriately modifying formula (4) above, and formulas (5) and (6) below.

Continuing with the example, a filter which corresponds to a wave speed of $c_{si}$ has an in-phase kernel:

$$ki(c_{si},r,t)=\sin(2\pi/\lambda_s*(n\Delta r-c_{si}*m\Delta t)); \quad \text{formula (5)}$$

and a quadrature kernel:

$$kq(c_{si},r,t)=\cos(2\pi/\lambda_s*(n\Delta r-c_{si}*m\Delta t)) \quad \text{formula (6)}$$

Here $\lambda_s$ is the wavelength of the shear wave 116.
The output of the filter is given by $$y(c_{si})=(\Sigma_{r,t}d(r,t)\times ki(c_{si},r,t))^2+(\Sigma_{r,t}d(r,t)\times kq(c_{si},r,t))^2 \quad \text{formula (7)}$$

An a priori estimate of $c_{si}$ is used in formulas (5) and (6) to derive the kernels of a first filter. The kernels are then applied to formula (7) to yield a first output. Other filters in the bank are generated by varying the value of $c_{si}$ in formulas (5) and (6), and recalculating $y(c_{si})$ in formula (7). The speed of the shear wave 116 is given by the value of $c_{si}$ for which $y(c_{si})$ has the maximum value.

Improved results may be obtained by windowing the kernel. This mitigates the bias caused by the truncation resulting from the finite extent of the kernels and sampled data (step S724).

With reference again to step S720, if, instead of the filter bank, a phase-difference-based wave speed calculation is to be made, input parameters to the calculation are derived. Specifically, the phases $\Phi$ are determined for the displacements 132. This can be done by Nyquist reconstruction based on the displacements 132 observed at a given spatial location 451, 452, 453, 454 . . . , and is performed for each of the different spatial locations. Phase differences $\Delta\Phi=\Phi_2-\Phi_1$ are calculated pair-wise to estimate the phase difference $\Delta\Phi$ to be substituted into formula (1). These phase difference calculations are performed for respective samples acquired at different times, as, for example, in the case of the temporally-first reconstructed A-line 444 and any subsequent one in the frame. The calculated phase differences $\Delta\Phi$ for differently-timed samples are corrected respectively using the inter-sample-delay-based phase correction 156 of $\omega\Delta t$. At least some of the pairs selected may be relatively far apart spatially, to improve accuracy of the calculations. Least-squares analysis can be used on the phase differences (corrected or uncorrected, as the case may be) and their respective inter-location distances 128 of $\Delta r$. Formula (1) (with or without the correction 156, as the case may be) is then applied to estimate the speed of the current wave component 116 (step S728).

With either path (i.e., through step S724 or S728), if the current wave component is not the last one to be subject to speed determination (step S732), the next component is made the current component (step S736).

If the same RF data used in wave speed determination for the previous component can be used for the current component, because, for example, the tracking pulse PRF 242 was sufficient for the highest harmonic (step S740), processing returns to step S712. Otherwise, if a further acquisition is to be made for the current component, processing returns, instead, to step S708.

In step S732, if the current wave component is, instead, the last one to be subject to speed determination, the Voigt model, which is well-known in the art, is applied to determine sheer elasticity and viscosity (step S744).

Shear wave dispersion ultrasound vibrometry (SDUV) is implemented in some embodiments to form, from a single tracking pulse, in-parallel-directed receive lines for making measurements of a monochromatic shear wave. In some embodiments, sampling is performed, over spatial locations by means of passes over the locations, in an interlaced pattern for making measurements of the wave. In some embodiments, measurements are made of the wave and to the measurements are applied a bank of filters that are tuned to respective candidate wave speeds, all without the need to determine a difference between wave phases at different spatial locations.

By extracting more information from each tracking pulse fired, methodology and apparatus as proposed herein afford a more complete sampling of the shear wave displacement field. This therefore allows for more robust estimation of the shear wave speed and the elastic properties of the medium.

The methods proposed herein can be implemented in software or, for example, in an article of manufacture inclusive of a device, which can be realized as one or more integrated circuits.

An embodiment employing RDT may be realized, for instance, as a single beamformer, such as a 16× or 32× multiline beamformer, hardware being added just for buffering, and the combining of overlapped receive lines.

It should be noted that the above-mentioned embodiments illustrate rather than limit the invention, and that those skilled in the art will be able to design many alternative embodiments without departing from the scope of the appended claims. For example, the methods disclosed herein may be implemented in any of various scanning geometries (linear, phased or curved). In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer having a computer readable medium. The mere fact that certain measures are recited in mutually different dependent claims does not indicate that a combination of these measures cannot be used to advantage.

What is claimed is:

1. A method for performing shear wave dispersion ultrasound vibrometry (SDUV), comprising:
   establishing a shear wave having a monochromatic shear wave component; and
   forming, from a single tracking pulse, a plurality of in-parallel-directed receive lines for making measurements of the monochromatic shear wave component, wherein the in-parallel-directed receive lines (i) are formed from echo data received from target locations after transmission of the single tracking pulse and (ii) comprise dynamically-formed receive lines that are spatially parallel.

2. The method of claim 1, further comprising:
from at least one other tracking pulse, executing said forming so as to overlap ones of a corresponding resulting plurality of in-parallel-directed receive lines to increase a measurement depth of field.

3. The method of claim 2, wherein increasing the measurement depth of field entails combining from among the overlapped ones of in-parallel-directed receive lines to create at least one reconstructed A-line.

4. The method of claim 3, wherein the at least one other tracking pulses includes differently-timed tracking pulses, further comprising:
forming, from the differently-timed ones of said at least one other tracking pulse, respective pluralities of reconstructed A-lines created by said combining.

5. The method of claim 1, wherein making measurements comprise making amplitude measurements of said monochromatic shear wave component at respective target locations.

6. An apparatus for performing shear wave dispersion ultrasound vibrometry (SDUV), comprising:
means for establishing a shear wave having a monochromatic shear wave component; and
means for forming, from a single tracking pulse, a plurality of in-parallel-directed receive lines for making measurements of a monochromatic shear wave component, wherein the in-parallel-directed receive lines (i) are formed from echo data received from target locations after transmission of the single tracking pulse and (ii) comprise dynamically-formed receive lines that are spatially parallel.

7. The apparatus of claim 6, wherein said single tracking pulse, and at least one other laterally-offset tracking pulse, are focused to a common depth, said apparatus further comprising:
means for, based on echo data from respective tracking pulses focused to said common depth, reconstructing a transmit focus at a shallower depth than said common depth.

8. The apparatus of claim 6, wherein said means for forming is further for forming, for at least one other tracking pulse, so as to overlap a corresponding resulting plurality of in-parallel-directed receive lines, further comprising means for interpolating pulse firing times of tracking pulses to correct for intersample wave propagation in determining a corresponding phase difference.

9. The apparatus of claim 6, wherein the apparatus is implemented as one or more integrated circuits.

10. A non-transitory computer readable medium embodying a computer program that includes instructions executable by a processor for performing shear wave dispersion ultrasound vibrometry (SDUV) via a plurality of acts, comprising:
establishing a shear wave having a monochromatic shear wave component; and
forming, from a single tracking pulse, a plurality of in-parallel-directed receive lines for making measurements of the monochromatic shear wave component, wherein the in-parallel-directed receive lines (i) are formed from echo data received from target locations after transmission of the single tracking pulse and (ii) comprise dynamically-formed receive lines that are spatially parallel.

* * * * *